United States Patent [19]

Weissmüller et al.

[11] Patent Number: 4,740,515

[45] Date of Patent: Apr. 26, 1988

[54] 3-(1,2,4-TRIAZOL-1-YL)-PROP-1-ENE FUNGICIDES

[75] Inventors: Joachim Weissmüller; Wolfgang Krämer, both of Wuppertal; Karl H. Büchel, Burscheid; Wilhelm Brandes, Leichlingen; Paul Reinecke, Leverkusen, all of Fed. Rep. of Germany

[73] Assignee: Bayer Aktiengesellschaft, Leverkusen, Fed. Rep. of Germany

[21] Appl. No.: 632,138

[22] Filed: Jul. 18, 1984

[30] Foreign Application Priority Data

Jul. 27, 1983 [DE] Fed. Rep. of Germany ....... 3327036

[51] Int. Cl.$^4$ .................... C07D 249/08; A01N 31/41
[52] U.S. Cl. .................................. 514/383; 514/184; 548/262
[58] Field of Search ............... 548/101, 262; 514/184, 514/383

[56] References Cited

U.S. PATENT DOCUMENTS

| | | | |
|---|---|---|---|
| 4,104,399 | 8/1978 | Pommer et al. | 548/262 |
| 4,315,017 | 2/1982 | Linhart et al. | 514/383 |
| 4,464,381 | 8/1984 | Janssen et al. | 514/383 |

FOREIGN PATENT DOCUMENTS

| | | | |
|---|---|---|---|
| 0052424 | 5/1982 | European Pat. Off. | 548/262 |
| 0056125 | 7/1982 | European Pat. Off. | 548/262 |
| 0057365 | 8/1982 | European Pat. Off. | 548/262 |
| 0060223 | 9/1982 | European Pat. Off. | 548/262 |
| 0063099 | 10/1982 | European Pat. Off. | 548/262 |
| 0094167 | 11/1983 | European Pat. Off. | 548/262 |
| 2547953 | 4/1977 | Fed. Rep. of Germany . | |
| 3130215 | 2/1983 | Fed. Rep. of Germany | 548/262 |
| 3218130 | 11/1983 | Fed. Rep. of Germany | 514/383 |

OTHER PUBLICATIONS

Stotskii et al., J. Org. Chem., USSR, vol. 19, pp. 1552–1554 (Eng. translation) (1983).
Chemical Abstracts, vol. 97, No. 7, 8/16/82, p. 644, col. 2, Abstract No. 55 738e.

Primary Examiner—Glennon H. Hollrah
Assistant Examiner—D. L. Dinner
Attorney, Agent, or Firm—Sprung Horn Kramer & Woods

[57] ABSTRACT 3-(1,2,4-Triazol-1-yl)-prop-1-enes of the general formula (I)

$$R^1-CH=C\begin{matrix}R^2\\C\\X^1\end{matrix}\begin{matrix}\\\\X^2\end{matrix}\begin{matrix}N=\!\!\!\!\!=\!\!\!\!\!N\\N\\N=\!\!\!\!\!=\!\!\!\!\!\end{matrix} \quad (I)$$

in which
  $X^1$ and $X^2$ independently of one another represent hydrogen or methyl,
  $R^1$ represents alkyl, alkenyl, in each case optionally substituted cycloalkyl or cycloalkenyl or in each case optionally substituted phenyl or benzyl and
  $R^2$ represents alkyl, alkenyl, in each case optionally substituted cycloalkyl or cycloalkenyl, halogenoalkyl, in each case optionally substituted phenyl or phenylalkyl, phenoxyalkyl or phenylthioalkyl, in each case optionally substituted in the phenyl part,
but wherein
  $R^1$ and $R^2$ may not simultaneously represent optionally substituted phenyl if $X^1$ and/or $X^2$ represent hydrogen,
and acid addition salts and metal salt complexes thereof which are tolerated by plants, exhibit fungicidal activity.

6 Claims, No Drawings

3-(1,2,4-TRIAZOL-1-YL)-PROP-1-ENE FUNGICIDES

The invention relates to new 3-(1,2,4-triazol-1-yl)-prop-1-enes, several processes for their preparation and their use as fungicides.

It has already been disclosed that, besides some azolylethyl compounds, such as, for example, 1-(2,6-dichlorobenzyloxy)-1-(4-chlorophenyl)-2-(1,2,4-triazol-1-yl)-ethane (compare DE-OS No. (German Published Specification) 2,547,953 [U.S. Pat. No. 4,327,104]), certain 3-azolyl-prop-1-enes, such as, for example, cis- or trans-1,2-bis-(2,4-dichlorophenyl)-3-(1,2,4-triazol-1-yl)-prop-1-ene (compare DE-OS No. (German Published Specification) 2,652,313) also have fungicidal properties.

However, in certain fields of indication, the action of these azole derivatives is not always completely satisfactory, especially when low amounts and concentrations are applied.

New 3-(1,2,4-triazol-1-yl)-prop-1-enes of the general formula (I)

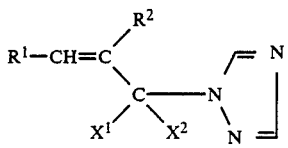
(I)

in which
$X^1$ and $X^2$ independently of one another represent hydrogen or methyl,
$R^1$ represents alkyl, alkenyl, in each case optionally substituted cycloalkyl or cycloalkenyl or in each case optionally substituted phenyl or benzyl and
$R^2$ represents alkyl, alkenyl, in each case optionally substituted cycloalkyl or cycloalkenyl, halogenoalkyl, in each case optionally substituted phenyl or phenylalkyl, phenoxyalkyl or phenylthioalkyl, in each case optionally substituted in the phenyl part, but wherein
$R^1$ and $R^2$ may not simultaneously represent optionally substituted phenyl if $X^1$ and/or $X^2$ represent hydrogen,
and acid addition salts and metal salt complexes thereof which are tolerated by plants, have been found.

The compounds of the formula (I) can be obtained as geometric isomers or isomer mixtures of varying composition. Both the pure isomers and the isomer mixtures are claimed according to the invention.

It has furthermore been found that the new 3-(1,2,4-triazol-1-yl)-prop-1-enes of the general formula (I) and acid addition salts and metal salt complexes thereof which are tolerated by plants are obtained by a process in which
(a) 3-halogeno- or 3-sulphonyloxy-prop-1-enes of the general formula (II)

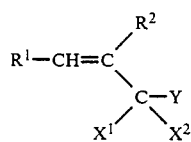
(II)

in which $R^1$, $R^2$, $X^1$ and $X^2$ have the abovementioned meaning and
Y represents halogen or optionally substituted alkylsulphonyloxy or arylsulphonyloxy,
are reacted with 1,2,4-triazole, if appropriate in the presence of a diluent and if appropriate in the presence of an acid-binding agent; or in which
(b) 1,2,4-triazol-1-ylmethyl ketones of the general formula (III)

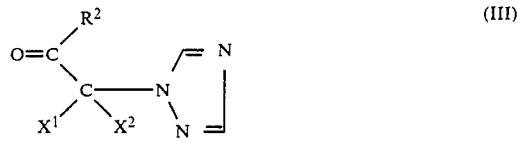
(III)

in which
$R^2$, $X^1$ and $X^2$ have the abovementioned meaning, are reacted with phosphonic acid esters or phosphine oxides of the general formnula (IVa)

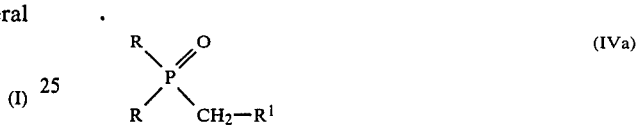
(IVa)

in which
$R^1$ has the abovementioned meaning and
R represents alkoxy or phenyl,
or, alternatively, with triphenylalkylidene-phosphoranes of the general formula (IVb)

$(C_6H_5)_3P=CH-R^1$ (IVb)

in which
$R^1$ has the abovementioned meaning,
in the presence of a diluent and in the presence of a base, in the sense of a "Wittig olefination".

If desired an acid or a metal salt can be added onto the compounds of the formula (I) thus obtained.

Finally, it has been found that the new 3-(1,2,4-triazol-1-yl)-prop-1-enes of the formula (I) have very good fungicidal properties.

Surprisingly, the active compounds of the formula (I) according to the invention exhibit a better fungicidal activity than the triazole compounds 1-(2,6-dichlorobenzyloxy)-1-(4-chlorophenyl)-2-(1,2,4-triazol-1-yl)-ethane or cis- or trans-1,2-bis-(2,4-dichlorophenyl)-3-(1,2,4-triazol-1-yl)-propene, which are known from the prior art and are closely related compounds chemically and from the point of view of their action. The substances according to the invention thus represent a valuable enrichment of the art.

Formula (I) provides a general definition of the 3-(1,2,4-triazol-1-yl)-prop-1-enes according to the invention. The 3-(1,2,4-triazol-1-yl)-1-propenes according to the invention are defined generally by formula (I).

3-(1,2,4-triazol-1-yl)-1-propenes of the general formula

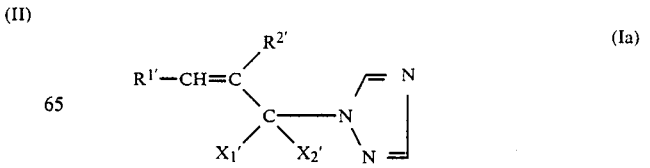
(Ia)

in which (a) if $X_1'$ and $X_2'$ simultaneously represent methyl, $R^{1'}$ represents alkyl, alkenyl, cycloalkyl or cycloalkenyl which are in each case optionally substituted or phenyl or benzyl which are in each case optionally substituted and $R^{2'}$ represents alkyl, alkenyl, cycloalkyl or cycloalkenyl which are in each case optionally substituted, halogenoalkyl, phenyl which is in each case optionally substituted or phenylalkyl, phenoxyalkyl or phenylthioalkyl which are in each case optionally substituted in the phenyl part, (b) if $X_1'$ represents hydrogen and $X_2'$ represents methyl, $R^{1'}$ represents alkyl, alkenyl, cycloalkyl or cycloalkenyl which are in each case optionally substituted, or phenyl or benzyl which are in each case optionally substituted, and $R^{2'}$ represents alkyl, alkenyl, cycloalkyl or cycloalkenyl which are in each case optionally substituted, halogenalkyl or phenylalkyl, phenoxyalkyl or phenylthioalkyl which are in each case optionally substituted in the phenyl part, (c) if $X_1'$ and $X_2'$ simultaneously represent hydrogen, $R^{1'}$ represents alkyl, alkenyl, cycloalkyl or cycloalkenyl which are in each case optionally substituted or phenyl or benzyl which are in each case optionally substituted, and $R^{1'}$ represnets alkyl with at least 5 carbon atoms, alkenyl, cycloalkyl or cycloalkenyl which are in each case optionally substituted, or the radical

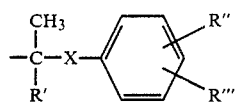

wherein $R'$ = alkyl ($C_1$-$C_4$),

R = H, halogen, OH, CN, $NO_2$, alkyl, alkoxy, alkylthio, halogenoalkyl, halogenoalkoxy, halogenoalkylthio or cycloalkyl, and X = $CH_2$, O, S, $CH_2$-O or $CH_2S$, are preferred.

The compounds of the formula (Ia) are prepared analogously to the compounds of the formula (I) in accordance with process variants (a) and (b) using compounds of the formula

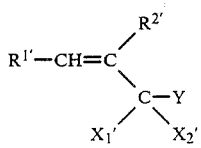

wherein $R^{1'}$, $R^{2'}$, $X_1'$ and $X_2'$ have the meaning given under formula (Ia) and Y represents halogen or optionally substituted alkylsulphonyloxy or arylsulphonyloxy, or using compounds of the formula

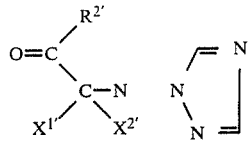

wherein $R^{2'}$, $X_1'$ and $X_2'$ have the above mentioned meaning. The following applies in the case of the radicals $R^{1'}$, $R^{2'}$, $X_1'$, $X_2'$, R'' and R''' unless otherwise defined in individual cases:

Alkyl preferably represents alkyl ($C_1$-$C_4$).

Alkenyl preferably represents alkenyl ($C_2$-$C_8$).

Optionally substituted cycloalkyl or cycloalkenyl preferably represent cycloalkyl ($C_3$-$C_7$) or cycloalkenyl ($C_5$-$C_8$) which are optionally substituted by halogen, alkyl ($C_1$-$C_4$), alkoxy ($C_1$-$C_4$), OH, CN or alkylthio ($C_1$-$C_4$).

Optionally substituted phenyl or benzyl preferably represent phenyl or benzyl which are optionally substituted by halogen, alkyl ($C_1$-$C_4$), alkoxy ($C_1$-$C_4$), OH, CN or alkylthio ($C_1$-$C_4$).

Halogenalkyl preferably represents alkyl ($C_1$-$C_4$) which is substituted by chlorine, bromine or fluorine.

Phenylalkyl which is optionally substituted in the phenyl part preferably represents phenylalkyl which has 1-4 C-atoms in the alkyl part and is optionally substituted in the phenyl part by halogen, alkyl ($C_1$-$C_4$) or alkoxy ($C_2$-$C_4$), and phenoxyalkyl and phenylthioalkyl preferably have 1-4 C-atoms in the alkyl part.

Halogen preferably represents F, Cl or Br. Preferred compounds of the formula (I) are those in which $X^1$ and $X^2$ independently of one another represent hydrogen or methyl, $R^1$ represents in each case straight-chain or branched alkyl or alkenyl with in each case up to 8 carbon atoms, cycloalkyl or cycloalkenyl with in each case 3 to 7 carbon atoms and in each case optionally mono- or poly-substituted by identical or different straight-chain or branched alkyl radicals with up to 4 carbon atoms, or phenyl or benzyl, in each case optionally mono- or poly-substituted by identical or different substituents, possible substituents being: hydroxyl, halogne, cyano, nitro, in each case straight-chain or branched alkyl, alkoxy or alkylthio with in each case up to 4 carbon atoms, halogenoalkyl, halogenoalkoxy or halogenoalkylthio with in each case 1 or 2 carbon atoms and 1 to 5 identical or different halogen atoms, cycloalkyl with 5 to 7 carbon atoms, dialkylamino, alkanoyloxy, alkoxycarbonyl, alkoxycarbonylamino or N-alkylalkoxycarbonylamino with in each case up to 4 carbon atoms in the individual straight-chain or branched alkyl parts, and phenyl or phenoxy, optionally mono- or poly-substituted by identical or different halogen atoms or straight-chain or branched alkyl radicals with up to 4 carbon atoms, and $R^2$ represents in each case straight-chain or branched alkyl or alkenyl with up to 8 carbon atoms, cycloalkyl or cycloalkenyl with in each case 3 to 7 carbon atoms and in each case optionally mono- or poly-substituted by identical or different straight-chain or branched alkyl radicals with up to 4 carbon atoms, a t-butyl radical which is mono- or polysubstituted by identical or different halogen atoms, phenyl, in each case optionally mono- or poly-substituted by identical or different substituents, or a phenylalkyl, phenoxyalkyl or phenylthioalkyl radical with in each case 1 to 5 carbon atoms in the straight-chain or branched alkyl part and optionally mono- or poly-substituted by identical or different substituents in the phenyl nucleus, possible substituents on the phenyl in each case being those mentioned for $R^1$;

but wherein $R^1$ and $R^2$ may not simultaneously represent optionally substituted phenyl if $X^1$ and/or $X^2$ represent hydrogen.

Particularly preferred compounds of the formula (I) are those in which $X^1$ and $X^2$ independently of one another represent hydrogen or methyl, $R^1$ represents methyl, ethyl, n- or i-propyl, n-, i-, s- or t-butyl, n-pentyl, neo-pentyl, n- or i-hexyl-, allyl, butenyl, or cyclopentyl, cyclohexyl, cyclohexenyl or cycloheptyl, in each case optionally mono- or poly-substituted by methyl, or phenyl or benzyl, in each case optionally mono-, di- or tri-substituted by identical or different substituents, particularly suitable substituents being: hydroxyl, fluorine, chlorine, bromine, cyano, nitro, methyl, methoxy, methylthio, methoxycarbonyl, trifluoromethyl, trifluoromethoxy, trifluoromethylthio, ethyl, ethoxy, ethylthio, ethoxycarbonyl, n- or i-propyl, isopropyloxy, n-, i-, s- or t-butyl, cyclohexyl, dimethylamino, diethylamino, acetoxy, acetamido, N-methylacetamido and phenyl or phenoxy which is mono-, di- or tri-substituted by identical or different fluorine, chlorine or methyl radicals, and $R^2$ represents methyl, ethyl, n- or i-propyl, n-, i-, s- or t-butyl, n- or i-pentyl, n- or i-hexyl, n- or i-heptyl, allyl, propenyl, butenyl, or cyclopentyl, cyclohexyl, cyclohexenyl or cycloheptyl, in each case optionally mono- or poly-substituted by methyl, the

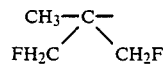

radical, phenyl or benzyl, in each case optionally mono-, di- or tri-substituted by identical or different substituents, or a

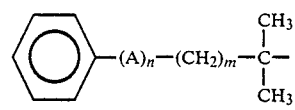

radical, which is mono-, di- or tri-substituted by identical or different substituents in the phenyl nucleus, possible substituents on the phenyl in each case being those mentioned for $R^1$;

wherein

A represents oxygen or sulphur, m represents the number 0, 1 or 2 and n represents the number 0 or 1.

Compounds of the formula (I) in which $R^1$ and $R^2$ simultaneously represent optionally substituted phenyl and at the same time $X^1$ and/or $X^2$ represent hydrogen are excluded.

The following compounds of the general formula (I) may be mentioned specifically, in addition to the compounds mentioned in the preparation examples:

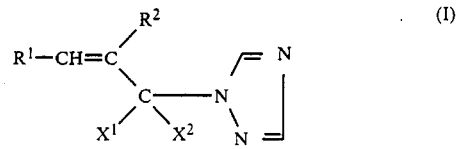

| $R^1$ | $R^2$ | $X^1$ | $X^2$ |
|---|---|---|---|
| CH₃ | Cl—⟨⟩—Cl | H | H |
| C₂H₅ | Cl—⟨⟩—Cl | H | H |
| n-C₃H₇ | Cl—⟨⟩—Cl | H | H |
| i-C₃H₇ | Cl—⟨⟩—Cl | H | H |
| n-C₄H₉ | Cl—⟨⟩—Cl | H | H |
| s-C₄H₉ | Cl—⟨⟩—Cl | H | H |
| t-C₄H₉ | Cl—⟨⟩—Cl | H | H |
| ⟨H⟩— | Cl—⟨⟩—Cl | H | H |
| ⟨H⟩— | Cl—⟨⟩—Cl | H | H |
| CH₃-⟨H⟩— | Cl—⟨⟩—Cl | H | H |
| ⟨H⟩— | Cl—⟨⟩—Cl | H | H |
| Cl—⟨⟩—Cl | CH₃—C(CH₂F)(CH₂F)— | H | H |

-continued $$R^1-CH=\overset{R^2}{\underset{\underset{X^2}{\overset{|}{C}}}{C}}-N\overset{N=CH}{\underset{CH=N}{\diagdown}} \quad (I)$$

| $R^1$ | $R^2$ | $X^1$ | $X^2$ |
|---|---|---|---|
| 3,5-Cl₂-C₆H₃ | (CH₃)C(CH₂F)₂ | H | H |
| 3,4-Cl₂-C₆H₃ | (CH₃)C(CH₂F)₂ | H | H |
| C₂H₅ | 4-Cl-C₆H₄-O-C(CH₃)₂- | H | H |
| n-C₃H₇ | 4-Cl-C₆H₄-O-C(CH₃)₂- | H | H |
| i-C₃H₇ | 4-Cl-C₆H₄-O-C(CH₃)₂- | H | H |
| n-C₃H₇ | 4-Cl-C₆H₄-O-C(CH₃)₂- | H | H |
| 2,4-Cl₂-C₆H₃ | 4-Cl-C₆H₄-O-C(CH₃)₂- | H | H |
| C₂H₅ | 4-Cl-C₆H₄-S-C(CH₃)₂- | H | H |
| n-C₃H₇ | 4-Cl-C₆H₄-S-C(CH₃)₂- | H | H |
| i-C₃H₇ | 4-Cl-C₆H₄-S-C(CH₃)₂- | H | H |
| 4-F-C₆H₄ | 4-Cl-C₆H₄-S-C(CH₃)₂- | H | H |
| n-C₃H₇ | 4-CH₃O-C₆H₄-S-C(CH₃)₂- | H | H |
| 3-F₃C-C₆H₄ | 4-CH₃O-C₆H₄-S-C(CH₃)₂- | H | H |
| C₂H₅ | 3,5-Cl₂-C₆H₃ | H | H |
| n-C₃H₇ | 3,5-Cl₂-C₆H₃ | H | H |
| i-C₃H₇ | 3,4-Cl₂-C₆H₃ | H | H |
| C₂H₅ | 3,4-Cl₂-C₆H₃ | H | H |
| 2,4-Cl₂-C₆H₃ | C₂H₅ | H | H |
| 2,4-Cl₂-C₆H₃ | n-C₃H₇ | H | H |
| 2,4-Cl₂-C₆H₃ | i-C₃H₇ | H | H |
| 2,4-Cl₂-C₆H₃ | n-C₇H₁₅ | H | H |
| C₆H₅-CH₂- | 4-Cl-C₆H₄-CH₂- | H | H |
| 4-Cl-C₆H₄-CH₂- | 4-Cl-C₆H₄-CH₂- | H | H |
| t-C₄H₉ | 4-Cl-C₆H₄-CH₂- | H | H |
| n-C₃H₇ | 4-Cl-C₆H₄-CH₂- | H | H |

-continued $$\underset{X^1\ \ X^2}{\overset{R^2}{\underset{|}{R^1-CH=C}}}\underset{}{\overset{}{\underset{|}{C}}}-N\underset{N}{\overset{N}{\diagdown}}\diagup\!\!\!=\!\!N \quad (I)$$

| $R^1$ | $R^2$ | $X^1$ | $X^2$ |
|---|---|---|---|
| ⌬—CH$_2$— | 2,3-Cl$_2$-C$_6$H$_3$-CH$_2$— | H | H |
| Cl—⌬—CH$_2$— | 2,3-Cl$_2$-C$_6$H$_3$-CH$_2$— | H | H |
| n-C$_3$H$_7$ | 2,3-Cl$_2$-C$_6$H$_3$-CH$_2$— | H | H |
| C$_2$H$_5$ | C$_6$H$_5$— | CH$_3$ | CH$_3$ |
| n-C$_3$H$_7$ | C$_6$H$_5$— | CH$_3$ | CH$_3$ |
| Cl—⌬—CH$_2$— | C$_6$H$_5$— | CH$_3$ | CH$_3$ |
| (CH$_3$)$_3$C—CH$_2$— | Cl—⌬— | H | H |
| H$_3$C— | O$_2$N—⌬— | H | H |
| Cl—⌬— | cyclohexyl | H | H |
| Cl—⌬— | H$_3$C—CH=CH— | H | H |
| n-C$_6$H$_{13}$ | CH$_3$ | H | H |
| n-C$_5$H$_{11}$ | —C(CH$_3$)=CH$_2$ | H | H |
| cyclopropyl | C$_2$H$_5$ | H | H |
| n-C$_3$H$_7$ | cyclohexenyl | H | H |
| Cl—⌬— | Cl—⌬—CH$_2$—C(CH$_3$)$_2$— | H | H |

-continued $$\underset{X^1\ \ X^2}{\overset{R^2}{\underset{|}{R^1-CH=C}}}\underset{}{\overset{}{\underset{|}{C}}}-N\underset{N}{\overset{N}{\diagdown}}\diagup\!\!\!=\!\!N \quad (I)$$

| $R^1$ | $R^2$ | $X^1$ | $X^2$ |
|---|---|---|---|
| ⌬— | 3,4-Cl$_2$-C$_6$H$_3$-CH$_2$-C(CH$_3$)$_2$— | H | H |
| Cl—⌬—CH$_2$— | CH$_3$ | CH$_3$ | CH$_3$ |

If, for example, 2-bromomethyl-1-(2,4-dichlorophenyl)-3,3-dimethylbut-1-ene and 1,2,4-triazole are used as starting substances, the course of the reaction in process (a) according to the invention can be represented by the following equation:

[reaction scheme: 2,4-dichlorophenyl-CH=C(C(CH$_3$)$_3$)(CH$_2$-Br) + 1,2,4-triazole →(-HBr) 2,4-dichlorophenyl-CH=C(C(CH$_3$)$_3$)(CH$_2$-N(triazolyl))]

If, for example, α-(1,2,4-triazol-1-yl)-isobutyrophenone and diethyl 2,4-dichlorobenzyl-phosphonate are used as starting substances, the course of the reaction in process (b) according to the invention can be represented by the following equation:

[reaction scheme: 2,4-dichlorophenyl-CH$_2$-P(=O)(OC$_2$H$_5$)$_2$ + O=C(C$_6$H$_5$)-C(CH$_3$)(CH$_3$)-N(triazolyl) →(base, -(C$_2$H$_5$O)$_2$P(=O)OH) 2,4-dichlorophenyl-CH=C(C$_6$H$_5$)-C(CH$_3$)(CH$_3$)-N(triazolyl)]

Formula (II) provides a general definition of the 3-halogeno- or 3-sulphonyloxy-prop-1-enes required as starting substances for carrying out process (a) according to the invention. In this formula (II), $X^1$, $X^2$, $R^1$ and $R^2$ preferably represent those radicals which have already been mentioned as preferred in the description of the corresponding radicals of the active compounds of the formula (I) according to the invention. Y preferably represents chlorine, bromine, methanesulphonyloxy or p-toluenesulphonyloxy.

3-Halogeno- or 3-sulphonyloxy-prop-1-enes of the formula (II) are known [compare, for example, Chemisches Zentralblatt 1927, II, 1811; and Compt. Rend. Sci. 232, 1762 (1951)].

They are obtained when allyl alcohol derivatives of the formula (V)

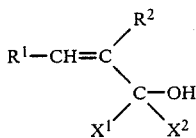

(V)

in which
  $R^1$, $R^2$, $X^1$ and $X^2$ have the abovementioned meaning,
are either reacted with halogenating agents, such as, for example, phosphorus pentachloride, phosphorus tribromide or thionyl chloride, in a known manner, if appropriate in the presence of a diluent, such as, for example, methylene chloride, chloroform or carbon tetrachloride, at temperatures between 0° C. and 80° C. to give the halogen derivatives of the formula (IIa)

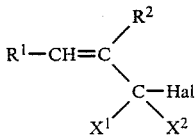

(IIa)

in which
  $R^1$, $R^2$, $X^1$ and $X^2$ have the abovementioned meaning and
  Hal represents halogen, in particular chlorine or bromine,
or are reacted with sulphonyl chlorides of the formula (VI)

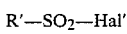

R'—SO$_2$—Hal'  (VI)

in which
  R' represents optionally substituted alkyl or aryl, in particular methyl or p-tolyl, and
  Hal' represents chlorine or bromine,
also in a known manner, if appropriate in the presence of a diluent, such as, for example, methylene chloride, and if appropriate in the presence of an acid-binding agent, such as, for example, pyridine, at temperatures between 20° C. and 100° C. to give the sulphonyloxy derivatives of the formula (IIb)

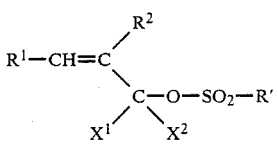

(IIb)

in which
  $R^1$, $R^2$, $X^1$, $X^2$ and R' have the abovementioned meaning.

Alternatively, compounds of the formula (IIa)

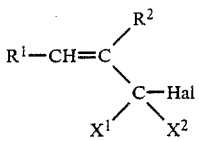

(IIa)

in which
  $R^1$, $R^2$, $X^1$, $X^2$ and Hal have the abovementioned meaning,
are obtained when ketones of the formula (VII)

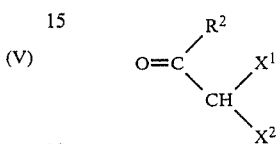

(VII)

in which
  $R^2$, $X^1$ and $X^2$ have the abovementioned meaning, are initially reacted in a 1st stage with phosphonic acid esters or phosphine oxides of the general formula (IVa)

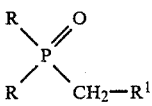

(IVa)

in which
  $R^1$ has the abovementioned meaning and
  R preferably represents methoxy, ethoxy or phenyl,
in the presence of a base, such as, for example, potassium t-butylate, and in the presence of a diluent, such as, for example, toluene, at temperatures between 50° C. and 150° C. in the sense of a "Wittig olefination" to give the olefins of the formula (VIII)

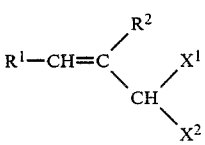

(VIII)

in which
  $R^1$, $R^2$, $X^1$ and $X^2$ have the abovementioned meaning, and these are halogenated in a 2nd stage in a known manner, for example with chlorine or with N-bromosuccinimide, if appropriate in the presence of a diluent, such as, for example, 1,1,2,2-tetrachloroethane or carbon tetrachloride, and if appropriate in the presence of a catalyst, such as, for example, azodiisobutyrodinitrile, at temperatures between 70° C. and 250° C.

Allyl alcohol derivatives of the formula (V)

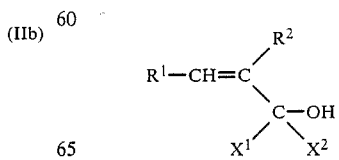

(V)

in which
  $R^1$, $R^2$, $X^1$ and $X^2$ have the abovementioned meaning, are obtained when α,β-unsaturated carboxylic acid esters or aldehydes of the formula (IX)

in which
R¹ and R² have the abovementioned meaning and
Z represents hydrogen or alkoxy, in particular methoxy or ethoxy, are reduced in the customary manner either with lithium aluminum hydride or with sodium borohydride, if appropriate in the presence of a catalyst, such as, for example, lithium iodide, if appropriate in the presence of a diluent, such as, for example, tetrahydrofuran, at temperatures between −20° C. and +50° C. to give the allyl alcohol derivatives of the formula (Va)

in which
R¹ and R² have the abovementioned meaning, or likewise are reacted in the customary manner with organimetallic methyl compounds, such as, for example, methyl-lithium or methyl-magnesium bromide, if appropriate in the presence of a diluent, such as, for example, ether, at temperatures between −80° C. and +50° C. to give the allyl alcohol derivatives of the formula (Vb)

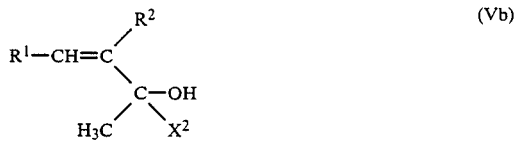

in which
R¹, R² and X² have the abovementioned meaning.

α,β-Unsaturated carboxylic acid esters or aldehydes of the formula (IX) are known and can be obtained analogously to known processes (compare, for example, Can. J. Chem. 49, 2143 [1971]; J. Amer. Chem. Soc. 80, 4949 [1958]; J. Chem. Soc. 1961, 3160; Liebigs. Ann. Chem. 658, 21 [1962]; Helv. chim. Acta 34, 1482 [1951]; J. Org. Chemistry 22, 33 [1957]; J. Amer. Chem. Soc. 69, 2605 [1947]; J. org. Chem. 16, 867 [1951]; J. Amer. Chem. Soc. 67, 1432 [1945]; J. org. Chemistry 23, 803 [1958]; J. Amer. Chem. Soc. 92, 226 and 6635 [1970]; J. org. Chemistry 26, 4278 [1961]; and J. Chem. Soc. 1969, 2799).

The phosphorus compounds of the formula (IVa) and (IVb) and the sulphonyl halides of the formula (VIII) are generally known compounds of organic chemistry.

Formula (III) provides a general definition of the 1,2,4-triazol-1-ylmethyl ketones required as starting substances for carrying out process (b) according to the invention. In this formula (III), R², X¹ and X² preferably represent those radicals which have already been mentioned as preferred in the description of the corresponding radicals of the active compounds of the formula (I) according to the invention.

The 1,2,4-triazol-1-ylmethyl ketones of the formula (III) are known (compare, for example, DE-OS No. (German Published Specification) 2,951,164 DE-OS No. (German Published Specification) 2,431,407 DE-OS No. (German Published Specification) 3,048,266; DE-OS No. (German Published Specification) 3,104,311; DE-OS No. (German Published Specification) 3,219,041; DE-OS No. (German Published Specification) 3,222,221 and DE-OS No. (German Published Specification) 3,232,737.

Possible diluents for process (a) according to the invention are inert organic solvents. These include, preferably, chlorinated hydrocarbons, such as, for example, methylene chloride, chloroform, carbon tetrachloride or chlorobenzene, amides, such as dimethylformamide, dimethylacetamide or N-methylformanilide, nitriles, such as acetonitrile or propionitrile, and the highly polar solvents dimethylsulphoxide, sulpholane or hexamethylphosphoric acid triamide.

Process (a) according to the invention can be carried out in the presence of an acid-binding agent. All the inorganic or organic acid-binding agents which can usually be employed may be added, such as alkali metal carbonates, for example sodium carbonate and potassium carbonate, such as lower tertiary alkylamines, cycloalkylamines or aralkylamines, for example triethylamine, N,N-dimethylcyclohexylamine and N,N-dimethylbenzylamine. An appropriate excess of 1,2,4-triazole is also possible.

The reaction temperatures can be varied within a substantial range in process (a) according to the invention. In general, the reaction is carried out between 0° C. and 150° C., preferably between 35° C. and 90° C.

For carrying out process (a) according to the invention, 1 to 30 mols of 1,2,4-triazole are preferably employed per mol of the compounds of the general formula (II). The compounds of the general formula (I) are isolated by customary methods.

Possible diluents for process (b) according to the invention are likewise inert organic solvents. These include, preferably, aliphatic or aromatic hydrocarbons, such as, for example, n- or i-butane, pentane, hexane, cyclohexane, benzene, toluene or xylene, ethers, such as, for example, diethyl ether, dimethoxyethane, tetrahydrofuran, dioxane or diethylene glycol dimethyl ether, amides, such as, for example, dimethylformamide, 2-pyrrolidone or hexamethylphosphoric acid triamide, and sulphoxides, such as, for example, dimethylsulphoxide.

Process (b) according to the invention is usually carried out in the presence of a base. Strong organic or inorganic bases are preferred, for example hydrides, such as lithium hydride, sodium hydride or calcium hydride, amides, such as sodium amide or lithium diisopropylamide, alcoholates, such as sodium methylate, sodium ethylate, potassium ethylate or potassium t-butylate, or organometallic compounds, such as methyl-lithium, propyl-lithium, butyl-lithium, phenyl-lithium, triphenylmethyl-sodium or mesityl-magnesium bromide.

The reaction temperatures can be varied within a substantial range in process (b) according to the invention. In general, the reaction is carried out between −20° C. and +150° C., preferably between 0° C. and 120° C.

For carrying out process (b) according to the invention, in general 1.0 to 1.3 mols, preferably equimolar amounts, of phosphonic acid ester or phosphine oxide of the formula (IVa) or 1.0 to 1.3 mols, preferably equimolar amounts, of triphenylalkylidene-phosphorane of the formula (IVb), and in general 1.0 to 2.0 mols, preferably 1.0 to 1.3 mols, of base are employed per mol of 1,2,4-triazol-1-ylmethyl ketone of the formula (III).

Usually, the phosphonic acid ester or the phosphine oxide of the formula (IVa) or the triphenylalkylidene-phosphorane of the formula (IVb) is taken together with the base in the corresponding diluent, and the 1,2,4-triazol-1-ylmethyl ketone of the formula (III), dissolved in a solvent, is added dropwise, while cooling the reaction mixture. When the addition has ended, the mixture is warmed to the required temperature to bring the reaction to completion. For working up and isolation of the reaction products of the formula (I), water is added to the reaction mixture, the mixture is extracted with an organic solvent and this is then distilled off, if necessary under reduced pressure.

The following acids can preferably be used for the preparation of physiologically acceptable acid addition salts of the compounds of the general formula (I): hydrogen halide acids, such as, for example, hydrochloric acid and hydrobromic acid, in particular hydrochloric acid, and furthermore phosphoric acid, nitric acid, sulphuric acid, monofunctional and bifunctional carboxylic acids and hydroxycarboxylic acids, such as, for example, acetic acid, maleic acid, succinic acid and fumaric acid, and sulphonic acids, such as, for example, p-toluenesulphonic acid and 1,5-naphthalenedisulphonic acid.

The acid addition salts of the compounds of the general formula (I) can be obtained in a simple manner by customary salt formation methods, for example by dissolving a compound of the formula (I) in a suitable organic solvent and adding the acid, for example hydrochloric acid, and they can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the general formula (I), examples of metals which may be mentioned being copper, zinc, manganese, magnesium, tin, iron and nickel.

Possible anions of the salts are those which are derived from the following acids: hydrogen halide acids, such as, for example, hydrochloric acid and hydrobromic acid, and furthermore phosphoric acid, nitric acid and sulphuric acid.

The metal salt complexes of the compounds of the general formula (I) can be obtained in a simple manner by customary processes, thus, for example, by dissolving the metal salt in alcohol, such as, for example, ethanol, and adding the solution to the compound of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as, for example, against the powdery mildew of cereal causative organism (*Erysiphe graminis*) or against the Net blotch disease of barley causative organism (*Pyrenophora teres*), and for combating fruit and vegetable diseases, such as, for example, against the apple scab causative organism (*Venturia inaequalis*) or against the powdery mildew of cucumber causative organism (*Sphaerotheca fuliginea*). The active compounds according to the invention are distinguished by an outstanding widespread action.

The active conpounds can be converted to the customary formulations, such as solutions, emulsions, wettable powders, suspensions, powders, dusting agents, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohenxane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as laolins, clays, talc, chalk, quartz, attapulgite, montmorillonite or diatomaceous earth, and ground synthetic minrtsld, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsuphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs and azo metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving the soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersiion, spraying atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

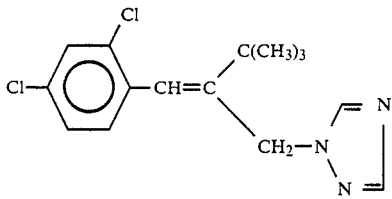

(Process a)

A mixture of 20 g (0.062 mol) of 2-bromomethyl-1-(2,4-dichlorophenyl)-3,3-dimethylbut-1-ene and 8.6 g (0.125 mol) of triazole in 80 ml of absolute acetonitrile is stirred at 40° C. for 16 hours. For working up, the reaction mixture is filtered, the filtrate is concentrated in vacuo and the residue is taken up in methylene chloride. The mixture is washed twice with water, dried over sodium sulphate and concentrated in vacuo. The syrup which remains is purified by chromatography (silica gel) and crystallized from petroleum ether. 4.6 g (24% of theory) of 1-(2,4-dichlorophenyl)-3,3-dimethyl-2-(1,2,4-triazol-1-ylmethyl)-but-1-ene of melting point 78° C. are obtained.

Preparation of the starting compound:

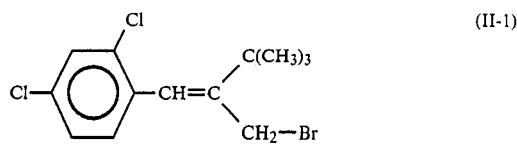

A mixture of 24.3 g (0.1 mol) of 1-(2,4-dichlorophenyl)-2,3,3-trimethylbut-1-ene, 17.8 g (0.1 mol) of N-bromosuccinimide and a spatula-tip of azodiisobutyrodinitrile in 100 ml of absolute 1,1,2,2-tetrachloroethane is boiled under reflux overnight. For working up, the mixture is concentrated in vacuo, the residue is taken up in carbon tetrachloride, the mixture is filtered and the filtrate is distilled. 20 g (62.1% of theory) of 2-bromomethyl-1-(2,4-dichlorophenyl)-3,3-dimethylbut-1-ene of boiling point 108° C. at 0.13 mbar are obtained.

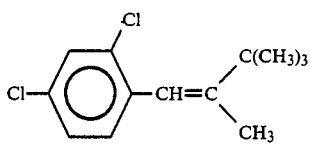

29.7 g (0.1 mol) of diethyl 2,4-dichlorobenzylphosphonate, 10 g (0.1 mol) of pinacolone, 12 g (0.1 mol) of potassium t-butylate and 300 ml of absolute toluene are heated at the boiling point in a nitrogen atmosphere for 20 hours. The solution is cooled, washed with 2 80 ml portions of water, dried over sodium sulphate and freed from the solvent in vacuo. After the residue has been distilled, 15 g (69.7% of theory) of 1-(2,4-dichlorophenyl)-2,3,3-trimethylbut-1-ene of boiling point 85° C. under 0.13 mbar are obtained.

EXAMPLE 2

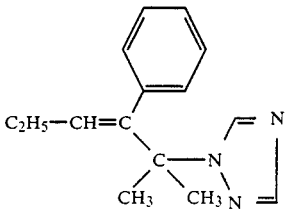

(Process b)

61 ml (0.1 mol) of a 15% strength solution of n-butyllithium in hexane are added dropwise to a suspension of 36.6 g (0.1 mol) of triphenyl-n-propyl-phosphonium bromide in 150 ml of absolute tetrahydrofuran at 0° C. under a nitrogen atmosphere and the mixture is subsequently stirred at 0° C. for 30 minutes. A suspension of 21.5 g (0.1 mol) of α-(1,2,4-triazol-1-yl)-isobutyrophenone in 150 ml of absolute tetrahydrofuran is then rapidly added dropwise and, when the addition has ended, the mixture is subsequently stirred at room temperature for a further 3.5 hours. It is then warmed at 40° C. for half an hour, the solvent is removed in vacuo, the residue is taken up in water and the mixture is extracted several times with chloroform. The combined organic phases are dried over sodium sulphate and evaporated in vacuo. The residue is taken up in petroleum ether and the mixture is heated to the boiling point and filtered.

After removal of the solvent from the filtrate in vacuo by distillation, 12.8 g (53% of theory) of 2-methyl-3-phenyl-2-(1,2,4-triazol-1-yl)-hex-3-ene of boiling point 98° C. to 100° C. under 0.13 mbar are obtained.

Preparation of the starting substances:

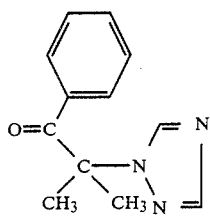

45.4 g (0.2 mol) of α-bromoisobutyrophenone and 1 g of potassium iodide are added to 14 g (0.2 mol) of triazole and 27 g (0.2 mol) of potassium carbonate in 100 ml of acetonitrile at 75° C. When the addition has ended, the mixture is stirred at 75° C. for a further 8 hours, filtered and rinsed with acetonitrile. The filtrate is concentrated, the residue is taken up in chloroform and the mixture is washed twice with water, dried over sodium sulphate and freed from the solvent in vacuo. The residue is recrystallized from ethyl acetate/petroleum ether. 12.1 g (28% of theory) of α-(1,2,4-triazol-1-yl)-isobutyrophenone of melting point 134° C. to 135° C. are obtained.

EXAMPLE 3

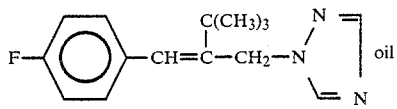

EXAMPLE 4

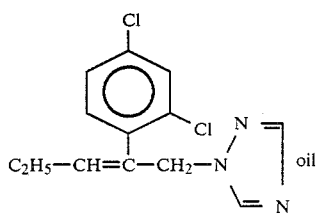

EXAMPLE 5

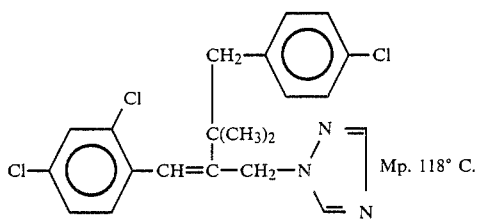

Use Examples:

The compounds listed below are used as comparison substances in the use examples which follow:

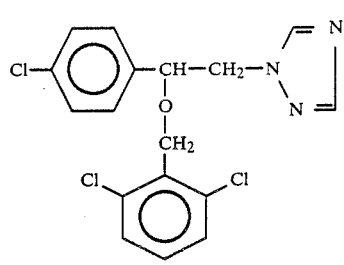

1-(4-Chlorophenyl)-1-(2,6-dichlorobenzyloxy)-2-(1,2,4-triazol-1-yl)-ethane

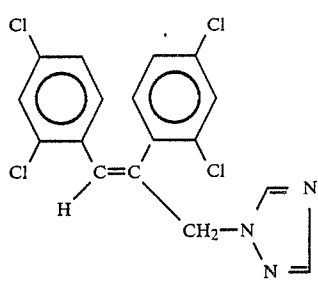

cis-1,2-Bis-(2,4-dichlorophenyl)-3-(1,2,4-triazol-1-yl)prop-1-ene

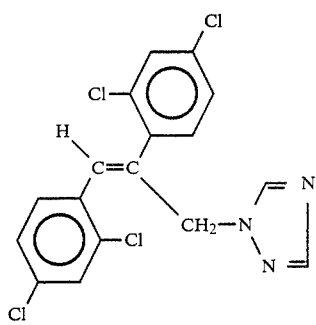

trans-1,2-Bis-(2,4-dichlorophenyl)-3-(1,2,4-triazol-1-yl)-prop-1-ene

EXAMPLE A

Erysiphe test (barley)/protective

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. *hordei*.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compound according to the following preparation example: 1.

EXAMPLE B

Venturia test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compound according to the following preparation example: 1.

EXAMPLE C

Sphaerotheca test (cucumber)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea*.

The plants are then placed in a greenhouse at 23° to 24° C. and at a relative atmospheric humidity of about 75%.

Evaluation is carried out 10 days after the inoculation.

In this test, a clearly superior activity compared with the prior art is shown, for example, by the compound according to the following preparation example: 1.

It will be understood that the specification and examples are illustrative but not limitative of the present invention and that other embodiments within the spirit and scope of the invention will sugggest themselves to those skilled in the art.

We claim:

1. A 3-(1,2,4-triazol-1-yl)-prop-1-ene of the formula (I) in which
    $X^1$ is hydrogen or methyl, or a plant-tolerated addition product thereof with an acid or metal salt,
    $R^1$ is alkyl with up to 8 carbon atoms, phenyl or mono- or di-halo phenyl,
    $R^2$ is alkyl with up to 8 carbon atoms, or phenyl which is optionally mono- or di-substituted by identical or different substituents selected from the group consisting of halogen, alkyl with 1 to 4 carbon atoms, alkoxy with 1 to 4 carbon atoms and phenyl is mono-substituted by halo-substituted phenyl,
    but with the proviso that $R^1$ and $R^2$ may not simultaneously represent optionally substituted phenyl.

2. A compound or addition product according to claim 1, in which
    $R^1$ represents methyl, ethyl, n- or i-propyl, n-, i-, s- or t-butyl, n-pentyl, neo-pentyl, n- or i-hexyl-, phenyl or phenyl which is mono-, or di-substituted by fluorine or chlorine.
    $R^2$ represents methyl, ethyl, n- or i-propyl, n-, or i-, s- or t-butyl, n- or i-pentyl, n- or i-hexyl, n- or i-heptyl, phenyl or phenyl which is mono- or di-substituted by identical or different substituents in the phenyl nucleus, possible substituents on the phenyl in each case being those mentioned for $R^1$:
    m represents the number 0, 1 or 2 and
    n represents the number 0 or 1,
    but with the proviso that $R^1$ and $R^2$ may not simultaneously represent optionally substituted phenyl if $X^1$ and/or $X^2$ represent hydrogen.

3. A compound according to claim 1, wherein such compound is 2-methyl-3-phenyl-2-(1,2,4-triazol-1-yl)-hex-3-ene of the formula

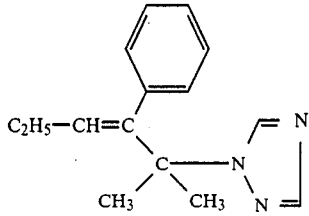

or a plant-tolerated addition product thereof with an acid or metal salt.

4. A fungicidal composition comprising a fungicidally effective amount of a compound or addition product according to claim 1 in admixture with a diluent.

5. A method of combating fungi which comprises administering to such fungi or to a fungus habitat a fungicidally effective amount of a compound or addition product according to claim 1.

6. A method according to claim 5 wherein such compound is 2-methyl-3-phenyl-2-(1,2,4-triazol-1-yl)-hex-3-ene, or a plant-tolerated addition product thereof with an acid or a metal salt.

UNITED STATES PATENT AND TRADEMARK OFFICE
CERTIFICATE OF CORRECTION

PATENT NO. : 4,740,515

DATED : April 26, 1988

INVENTOR(S) : Joachim Weissmüller, et al.

It is certified that error appears in the above-identified patent and that said Letters Patent is hereby corrected as shown below:

| | |
|---|---|
| Col. 3, line 32 | Delete "$R_2^{1'}$ represnets" and substitute --$R^{2'}$ represents-- |
| Col. 4, line 48 | Correct spelling of --halogen-- |
| Col. 13, line 30 | Correct spelling of --organometallic-- |
| Col. 16, lines 53-54 | Delete "laolins" and substitute --kaolins-- |
| Col. 17, line 29 | Correct spelling of --immersion-- |
| Col. 22, lines 1 to 16 | Delete claim 1 in its entirety and substitute: |

-- 1. A 3-(1,2,4-triazol-1-yl)-prop-1-ene of the formula (I)

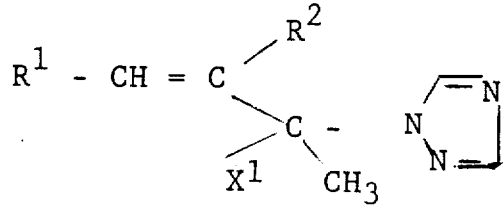

in which $X^1$ is hydrogen or methyl, $R^1$ is alkyl with up to 8 carbon atoms, phenyl, or mono- or di-halo phenyl, $R^2$ is alkyl with up to 8 carbon atoms, or phenyl which is optionally mono- or di-substituted by identical or different substituents selected

UNITED STATES PATENT AND TRADEMARK OFFICE
CERTIFICATE OF CORRECTION

PATENT NO. : 4,740,515
DATED : April 26, 1988
INVENTOR(S) : Joachim Weissmüller, et al.

It is certified that error appears in the above-identified patent and that said Letters Patent is hereby corrected as shown below:

from the group consisting of halogen, alkyl with 1 to 4 carbon atoms, alkoxy with 1 to 4 carbon atoms and phenyl,
but with the proviso that $R^1$ and $R^2$ may not simultaneously represent optionally substituted phenyl, or a plant-tolerated addition product thereof with an acid or metal salt.--

Signed and Sealed this

Fifteenth Day of November, 1988

Attest:

DONALD J. QUIGG

*Attesting Officer*  *Commissioner of Patents and Trademarks*